(12) United States Patent
Moy et al.

(10) Patent No.: US 8,855,397 B2
(45) Date of Patent: Oct. 7, 2014

(54) METHOD FOR DETECTING CLUSTERS OF BIOLOGICAL PARTICLES

(75) Inventors: Jean-Pierre Moy, Saint Egreve (FR); Mathieu Dupoy, Grenoble (FR); Olivier Figadere, Villebois (FR); Frédéric Pinston, Grenoble (FR); Geneviève Bossy, Ambérieu en Bugey (FR); Laurent Drazek, Grenoble (FR); Maryse Guicherd, Vézéronce Curtin (FR); Fabien Romanens, Grenoble (FR); Frédéric Mallard, Voreppe (FR)

(73) Assignees: Commissariat a l'Energie Atomique et aux Energies Alternatives, Paris (FR); Biomerieux, Marcyl'Etoile (FR)

(*) Notice: Subject to any disclaimer, the term of this patent is extended or adjusted under 35 U.S.C. 154(b) by 178 days.

(21) Appl. No.: 13/639,593

(22) PCT Filed: Apr. 6, 2011

(86) PCT No.: PCT/IB2011/051481
§ 371 (c)(1),
(2), (4) Date: Dec. 17, 2012

(87) PCT Pub. No.: WO2011/125033
PCT Pub. Date: Oct. 13, 2011

(65) Prior Publication Data
US 2013/0084598 A1    Apr. 4, 2013

(30) Foreign Application Priority Data
Apr. 6, 2010    (FR) ..................... 10 01406

(51) Int. Cl.
G06K 9/00    (2006.01)
C12Q 1/04   (2006.01)
C12Q 1/06   (2006.01)

(52) U.S. Cl.
CPC ............ C12Q 1/04 (2013.01); G01N 2333/195 (2013.01); C12Q 1/06 (2013.01)
USPC ........................................ 382/133; 382/225

(58) Field of Classification Search
USPC ............ 356/129, 237.4, 237.5, 518; 359/346; 382/133, 225; 702/5; 705/737, 705/E17.046, E17.047, E17.089, E17.092
See application file for complete search history.

(56) References Cited

U.S. PATENT DOCUMENTS 3,468,610 A     9/1969  Muffoletto
6,587,792 B1 *  7/2003  Thomas .................... 702/26
(Continued)

FOREIGN PATENT DOCUMENTS

| FR | 2 738 343 A1 | 3/1997 |
| JP | 59 166842 A | 9/1984 |
| WO | WO 95/00661 A1 | 1/1995 |
| WO | WO 99/24786 A1 | 5/1999 |
| WO | WO 2004/005537 A1 | 1/2004 |

OTHER PUBLICATIONS

Wang H et al.; "Effect of Surface Roughness on Retention and Removal of *Escherichia coli* 0157:H7 on Surfaces of Selected Fruits"; Journal of Food Science 2009; Jan.-Feb. PubMed: 19200095; vol. 74, No. 1, Jan. 2009; pp. E8-E15; XP002601176.*

(Continued)

*Primary Examiner* — Gregory F Cunningham
(74) *Attorney, Agent, or Firm* — Alston & Bird LLP

(57) ABSTRACT

The invention relates to a method for detecting clusters of biological particles (12) on a surface (11), comprising steps that involve: a. determining (E1) a topographical representation (20) of said surface; and b. detecting (E3, E4), on said topographical representation, at least one contour defining a region that is likely to correspond to a cluster of biological particles.

12 Claims, 8 Drawing Sheets

(56) References Cited

U.S. PATENT DOCUMENTS

2003/0036208 A1* 2/2003 Rohrwasser et al. ......... 436/536
2009/0060134 A1 3/2009 Fuller
2011/0182494 A1* 7/2011 Sokolov et al. ............... 382/133

OTHER PUBLICATIONS

Verran J et Al.; "The Retention of Bacteria on Hygienic Surfaces Presenting Scratches of Microbial Dimensions"; Letters in Applied Microbiology; Mar. 2010; Pubmed: 20070506; vol. 50, No. 3; Mar. 2010; pp. 258-263; XP002601175.*

International Search Report from International Patent Application No. PCT/IB2011/051481, dated Jul. 7, 2011.
Written Opinion form International Patent Application No. PCT/IB2011/051481, dated Jul. 7, 2011.
International Preliminary Report on Patentability from International Patent Application No. PCT/IB2011/051481, dated Oct. 9, 2012.
Verran J et al.; "The Retention of Bacteria on Hygienic Surfaces Presenting Scratches of Microbial Dimensions"; Letters in Applied Microbiology; Mar. 2010; Pubmed 20070506; vol. 50, No. 3; Mar. 2010; pp. 258-263; XP002601175.

* cited by examiner

METHOD FOR DETECTING CLUSTERS OF BIOLOGICAL PARTICLES

FIELD OF THE INVENTION

The invention relates to a method of detecting clusters of biological particles, such as microorganisms (bacteria, yeasts, fungi, . . . ) or of vegetable or animal cells, on a surface, e.g. a surface of a culture medium or of a functionalized substrate. Such particles present dimensions that are microscopic, typically being of the order of 0.5 µm to 3 mm, and more particularly lying in the range 0.5 µm to 10 µm.

The invention applies in particular to detecting colonies of microorganisms.

BACKGROUND

In numerous applications, it is desired to detect as soon as possible the growth of microorganisms such as bacteria or yeasts on a culture medium, usually a nutrient gel surface. In general, the surface of the gelose culture medium departs significantly from being accurately planar, since it frequently presents local depth defects of a few micrometers (µm) extending over distances of a few millimeters (mm). Dust or debris conveyed together with the sample may also give rise to local surface deformations that present high spatial frequencies.

Bacteria and yeasts are difficult to identify at the beginning of their growth, since they absorb very little light in the visible, the near ultraviolet, or the near infrared, and since their refractive index is very close to that of the surrounding medium. Thus, typically only colonies presenting a diameter greater than 100 µm can be detected by the naked eye; the time needed for colonies to grow to such dimensions is typically of the order of 6 hours (h) to 24 h.

Examination with a high power microscope, preferably against a black background, is one possible approach, but it is difficult to implement.

Other techniques are commonly used.

For example, it is possible to make the microorganisms fluorescent by means of various non-fluorescent additives that are transformed by the metabolism of the microorganisms into fluorescent substances, which substances are selected to remain inside the microorganisms for a long time. That method requires a considerable amount of time (greater than 5 h) before the bacteria become fluorescent, and it also requires fluorescent-generating metabolites to be developed.

Similarly, color-generating media enable microorganisms to be viewed in selective manner, but the same problem arises: staining requires a considerable length of time (several hours) before it is visible to the naked eye.

Furthermore, all of those methods run the risk of leading to serious disturbances of the metabolism of microorganisms, while subsequent tests (e.g. measuring sensitivity to antibiotics) require microorganisms to be developed under the most favorable possible conditions.

SUMMARY

The invention seeks to mitigate the above-mentioned drawbacks by providing a method of detecting cultures of biological particles that includes as little as possible and that makes it possible to achieve early detection of clusters of small dimensions, such as colonies of microorganisms at the beginning of their growth.

In accordance with the invention, such an object is achieved by a method of detecting a cluster of biological particles on a surface, the method comprising the steps consisting in:

a) determining a topographical representation of said surface; and b) detecting in said topographical representation at least one contour defining a region that potentially corresponds to a cluster of biological particles.

These steps are implemented using a suitably-programmed computer or other electronic data processor means, in association with an appropriate measuring device (in particular for performing step a)).

In advantageous implementations of the invention:

Said biological particles may be selected from microorganisms, such as bacteria, yeasts, or fungi, and vegetable or animal cells.

Said biological particles may present a diameter or a main dimension lying in the range 10 µm to 3 mm, or preferably less than or equal to a few hundreds of 100 µm, e.g. less than or equal to 100 µm.

Said surface may be selected from: the interface between a culture medium and a surrounding medium such as air; the surface of a functionalized substrate; and the surface of a microporous membrane.

Said step a) consisting in determining a topographical representation of said surface may be implemented by an optical method that is performed without contact and without preparing the sample so as to guarantee minimum intrusiveness. In particular, it may be constituted by a method of chromatic confocal microtopography, or else Schlieren photography, or ombroscopy.

Said step b) may consist in detecting at least one contour is implemented by measuring the local slope of said topographical representation of the surface, with thresholding.

The method may also include an operation of preprocessing said topographical representation, the preprocessing operation comprising detecting a reference surface and subtracting it.

The method may include repeating steps a) and b) at successive times, and selecting only those regions identified in the steps b) that are of shape or size that varies over time.

In an advantageous variant of the invention, the method may include an additional step c) consisting in quantifying an indicator relating to the size of a detected cluster, e.g. to its volume. This is particularly advantageous when the mean size of the biological particles in question is known. Under such circumstances, this step c) makes it possible to evaluate the quantities of biological particles present in the clusters. Knowing the mean size of the biological particles of interest, taken individually, it is easy, once the size of a cluster has been determined, to quantify the number of biological particles present in said cluster. Such a variant of the invention is particularly advantageous when the biological particles are microorganisms and subsequent treatment of said microorganisms is envisaged, in which case it is necessary to take a sample from the colony. This variant thus makes it possible to ensure that the quantity of microorganisms present is sufficient, e.g. before taking a sample.

BRIEF DESCRIPTION OF THE DRAWINGS

In an advantageous variant of the invention, the method may include an additional step of in-situ or ex-situ identification of the microorganisms arranged in clusters.

Other characteristics, details, and advantages of the invention appear on reading the following description made with reference to the accompanying drawings given by way of example, in which.

DETAILED DESCRIPTION

Figure 1:
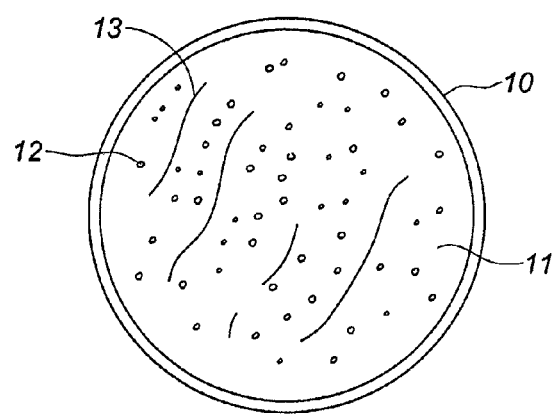
FIG. 1 shows the surface of a culture medium having colonies of bacteria present thereon.

FIG. 1 shows a plan view of a Petri dish 10; the dish contains a nutrient medium (gelose) with colonies of bacteria 12 that have developed on its surface 11. The method of the invention seeks to detect these colonies at an early stage in their growth, when they are of a diameter that is too small for them to be visible to the naked eye (a diameter of a few tens of micrometers, e.g. 30 µm or less). The surface 11 of the culture medium (i.e. the gelose-air interface) presents irregularities 13 associated with the surface state of the gelose. In the example of FIG. 1, the gelose is exposed directly to air; consequently, it tends to dry, thereby leading to modifications to its surface, and in particular to variations in its mean level. Advantageously, a method of detecting a cluster of biological particles on an gelose surface takes these surface irregularities into consideration, as well as the modifications to which the surface is subjected.

The method of the invention makes use of the known fact that the multiplication of bacteria at the surface of a nutrient medium forms a protuberance. The height of this protuberance during the initial stages of the growth of the colony is of the order of hundreds of nanometers or of the order of micrometers. The idea on which the invention is based consists in detecting the protuberances associated with the clusters of biological particles using already-known surface topography techniques, associated with appropriate image processing.

Figure 2:
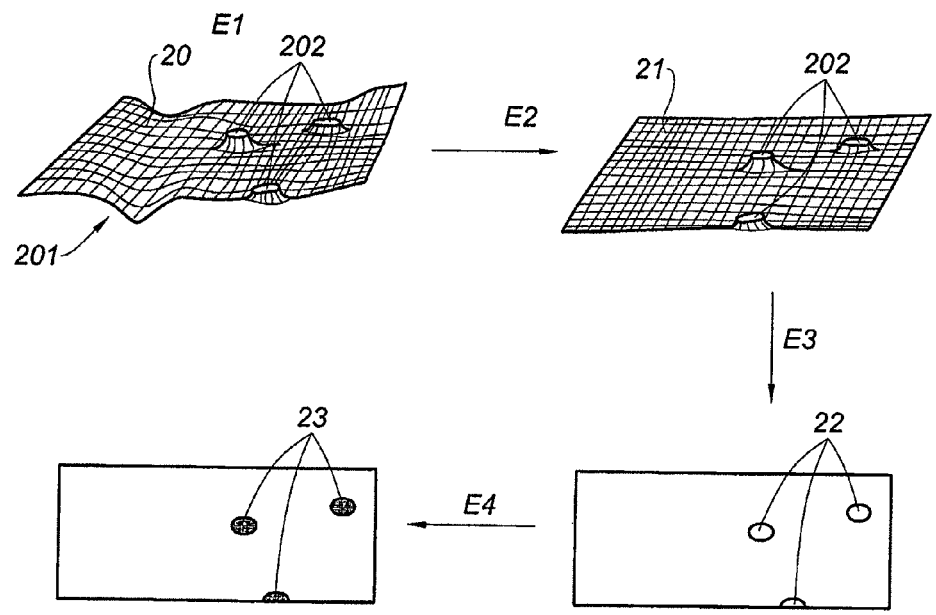
FIG. 2 is a diagram showing the various steps of a method in an implementation of the invention.

As shown in FIG. 2, the first step E1 of the method of the invention consists in determining a topographical representation 20 of the surface 11 on which the clusters 12 for detection are developing. In the example shown in this figure, the topographical representation is three-dimensional, and in particular it is in the form of a "three-dimensional sheet". Each point of the surface has coordinates (x,y) in an Oxy plane and is associated in a three-dimensional topographical representation with a z coordinate along an axis Oz that is preferably perpendicular to the Oxy plane. This representation may be in the form of a three-dimensional surface in an Ox, Oy, Oz frame of reference or in the form of a matrix in which the elements $a_{i,j}$ correspond to the heights along the z axis of the points having coordinates (i,j) in the Oxy plane.

The second step E2 is an operation of preprocessing the topographical representation 20, which operation includes detecting and subtracting a base surface. As explained above, the surface 11 may be poorly defined and may even vary over time. In order to ensure good detection of clusters of particles, it is necessary to determine a base surface that is extracted by appropriate data processing, e.g. lowpass spatial filtering, with a cutoff frequency that is typically of the order of 0.001 per micrometer ($\mu m^{-1}$), and for example lies in the range 1/2000 $\mu m^{-1}$ to 1/500 $\mu m^{-1}$. The scratches due to preparing the culture medium, variations in thickness, even non-uniform variations, and departures from planarity all disappear.

In a more simple variant, a mean slope is calculated in the vicinity of a region of the surface in order to determine a base surface that is plane and inclined.

Reference 21 designates the filtered three-dimensional sheet (more generally: the topographical representation), in which irregularities 201 of low spatial frequency (e.g. due to irregularities of the culture medium 13) have been eliminated by the above-described processing operation. All that remains on the sheet 21 are irregularities and roughnesses 202 of size that is sufficiently small and/or that contain spatial frequencies that are sufficiently high. The term "high" is used of a spatial frequency to mean frequencies greater than 1/500 $\mu m^{-1}$. It is possible to eliminate components at very high frequencies, i.e. components corresponding to spatial frequencies greater than a few $\mu m^{-1}$, where such components correspond to the roughness of the gel constituting the culture medium.

The third step E3 consists in extracting contours 22 from the three-dimensional sheet 21. In known manner, the contours can be detected by contour detector filters that are known to the person skilled in the art, by measuring the local slope of the sheet, followed by thresholding, or by bandpass spatial filtering, e.g. a filter having a passband lying in the range a few 1/500 $\mu m^{-1}$ to a few 1/10 $\mu m^{-1}$. At least some of the contours 22 define closed regions 23 that are identified in the fourth step E4 as possibly corresponding to clusters of biological particles. The step E4 may comprise an operation of selecting closed regions to be taken into consideration. For example, it is possible to apply a selection criterion whereby only regions of dimensions that are sufficiently small (diagonal or diameter of the order of a few tens of micrometers) are retained as potentially representing clusters of biological particles. In a variant, or in combination, it is possible to repeat the steps E1-E4 at successive times, and to select only those regions 22 that are of shape or size that varies over time. Clusters of biological particles are "living" structures that change over time, whereas non-biological structures change very little if at all between two successive measurements. This also makes it possible to measure the rate of growth of the clusters.

The first step E1 of the method, which consists in determining a topographical representation of the surface on which the clusters for detection develop, may be implemented by applying various different microtopographical techniques that are themselves known. In order to avoid disturbing the growth of the clusters that are to be detected, it is particularly preferred to make use of techniques that do not involve contact, in particular optical techniques that do not involve preparing the sample (i.e. that do not rely on using dyes, fluorophores, or precursors thereof).

In general, an optical microtopographical technique comprises:

using a light source to illuminate the surface for which a three-dimensional representation is to be obtained;
  using a light sensor to detect a signal corresponding to the light reflected or transmitted by the surface; and
  determining a three-dimensional topographical representation of the surface from the detected signal.

The illumination of the surface may be directed from the surrounding medium towards the surface. When the illumination is not collimated, it may be focused on the zone that is to be measured. The light source may be coherent in space and/or time, or it may be incoherent. It may be polychromatic or monochromatic. Detection may be performed by a one-dimensional image sensor (strip) or a two-dimensional image sensor (matrix) of the complementary metal oxide-on-silicon (CMOS), charge-coupled device (CCD), photomultiplyer, photodiode, etc. type. The sensor may have a spectrometric function enabling the spectrum of the detected light to be analyzed. It may also be coupled with a diaphragm, or "pinhole", in order to constitute a confocal detector device.

Two techniques are described in detail below as constituting preferred implementations of the invention. Nevertheless, other optical techniques may also be applied to the method of the invention, for example: automatically focusing on the surface by auto-collimation or by image processing; interferometric and/or holographic methods; analyzing the reflection wave front; etc.

The first microtopographical optical technique that has been successfully applied to early detection of clusters of biological particles on a surface is chromatic confocal microtopography. Chromatic confocal microtopography has been developed by the supplier Stil S.A. and is described in detail in document FR 2 738 343.

Figure 3:
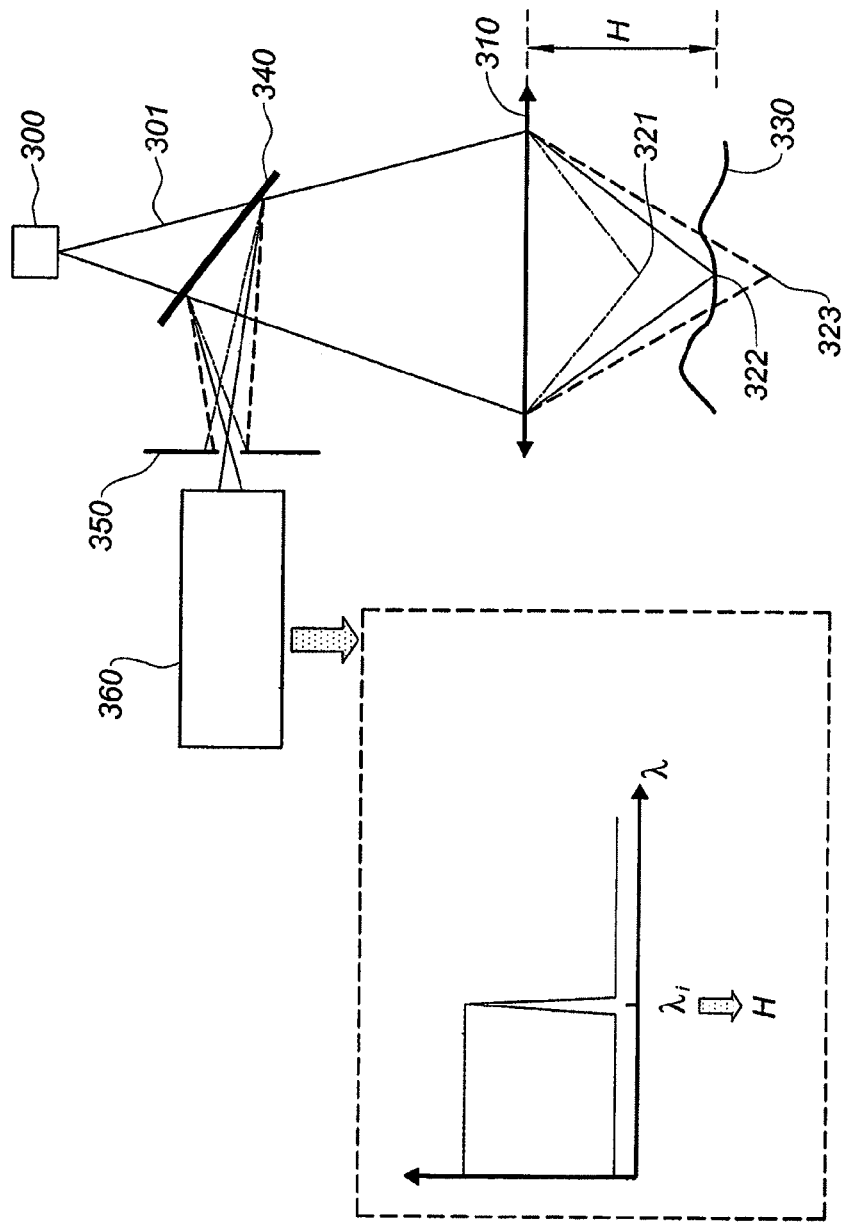
FIG. 3 illustrates the principle of chromatic confocal microtopography that is used in a first variant of the method of the invention.

The chromatic confocal microtopography technique—or chromatic confocal imaging—is shown in FIG. 3.

A point source 300 of white light (or in any event of polychromatic light), e.g. implemented in the form of an extensive source associated with a pinhole, emits a light beam 301 that is focused by an objective lens 310. This lens 310 presents extended axial chromatism: consequently, the various spectral components of the beam 301 are focused at respective focal points 321, 322, 323, . . . that are spaced along the optical axis of the lens. The beam as focused in this way at normal incidence is directed onto the surface 330 of a sample. The light reflected by the surface 330 passes a second time through the lens 310, this time propagating towards the source 300; a fraction of the reflected light is extracted by a beam splitter 340 that is directed towards an axially movable pinhole 350 arranged in front of a spectrophotometer 360. This performs spatial filtering: only light rays that come from a point conjugate with the pinhole 350 are able to reach the spectrophotometer 360. Because of the axial chromaticity of the lens 310, these light rays present respective well-defined wavelengths $\lambda_i$ that depend on the distance H between the lens 310 and the reflective surface 330. It is thus possible to determine H from the wavelength $\lambda_i$ as measured by the spectrophotometer 360.

A topographical representation of the surface 330 can thus be obtained by scanning.

The use of this technique for implementing the method of the invention has been demonstrated experimentally by using a seeded gelose culture medium and an optical system characterized by:
- a sampling frequency of 1 kilohertz (kHz);
- a distance dynamic range of about 300 µm; and
- a spectrophotometer using a 1000 pixel CCD strip as its detector, each pixel coding a height of 300 nanometers (nm).

Signal processing methods, e.g. super-pixelzation, make it possible to obtain vertical resolution that is smaller than 300 nm. Such known methods serve to improve resolution by combining the contents of adjacent pixels.

By way of example, it is possible to use the Altisurf 500 apparatus from the supplier Altimet.

Figure 4A:
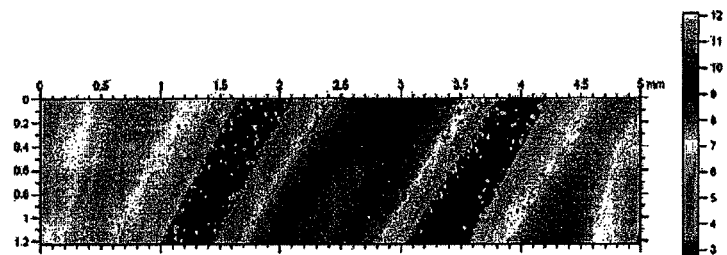
FIGS. 4A & 4B and 5A, 5B, 5C, 5D & 5E show experimental results obtained by applying the technique of chromatic confocal microtopography to a culture medium seeded with bacteria.
Figure 4B:
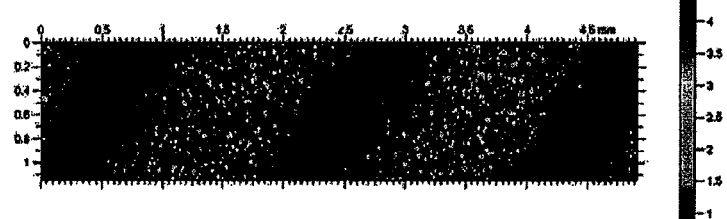

The experimental results are shown in FIGS. 4A and 4B, and also in FIGS. 5A to 5E. In these figures, the three-dimensional sheet is replaced by a representation that is entirely equivalent and that makes use of a gray scale (dark gray for low altitudes, pale gray or white for higher altitudes).

FIG. 4A is a topographical representation of the surface of an gelose culture medium seeded by *Staphylococcus epidermidis*. It may be observed that the surface is distorted over several tens of micrometers in the form of stripes. FIG. 4B shows the same representation after preprocessing to subtract a base surface. The surface distortion has disappeared, but there is no difficulty in observing colonies of bacteria having a height of about 2 µm, and diameters lying in the range 10 µm to a few hundreds of µm. Thereafter, the colonies were identified automatically by calculating the local slope and thresholding. The size of the gelose surface under study in this example was 1.2 mm×5 mm.

Figure 5A:
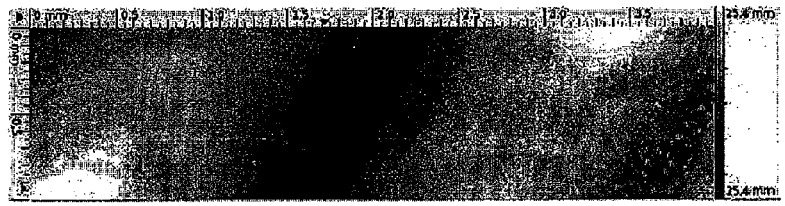
Figure 5B:
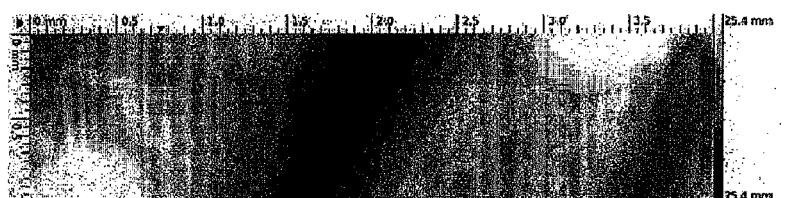
Figure 5C:
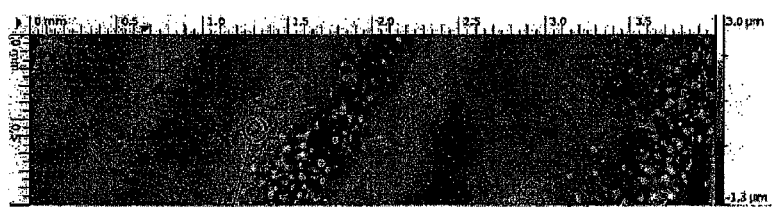

FIG. 5A is a topographical representation of the surface of another gelose culture medium seeded with *Escherichia coli*, prior to subtracting the background. FIG. 5B shows the background surface, revealing surface irregularities in the form of stripes, and FIG. 5C shows the surface after the background has been subtracted, with colonies of bacteria being clearly visible therein.

Figure 5D:
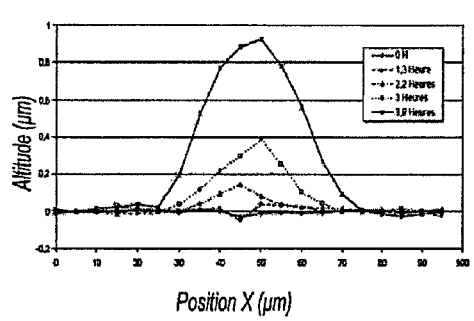
Figure 5E:
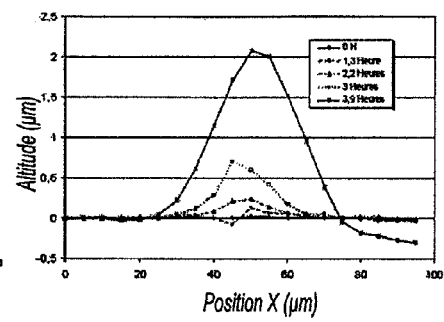

FIGS. 5D and 5E show variation over time (at times 0; 1.3 h; 2.2 h; 3 h; 3.9 h) of the one-dimensional profiles of two of those colonies. It can be seen that the colonies become detectable after about 2 h, and that it is possible to follow their rate of growth.

In this method, the representation of the topography of the surface of the medium is a three-dimensional representation. The contours that are detected correspond to closed loops defining a volume. Depending on the contour detection method used, the closed loops interconnect pixels that correspond either to a slope that is the same or else to an altitude that is the same.

Each volume defined by a contour may be quantified by an indicator, which indicator may comprise the integral of the weight (i.e. the height) of the pixels included in said volume. While calculating this integral, the weights of the pixels may be subjected to thresholding. In other words, account is taken only of weight values that exceed a certain threshold. This threshold may be established on the basis of the weight of one or more pixels constituting the contour, or the weight of one or more pixels distributed over a surface area defined by the contour.

When the type of microorganism constituting the volume is known, this indicator makes it possible to estimate its biomass.

In another implementation, the clusters of biological particles are detected by a Schlieren photography method, also known as "strioscopy".

Figure 6A:
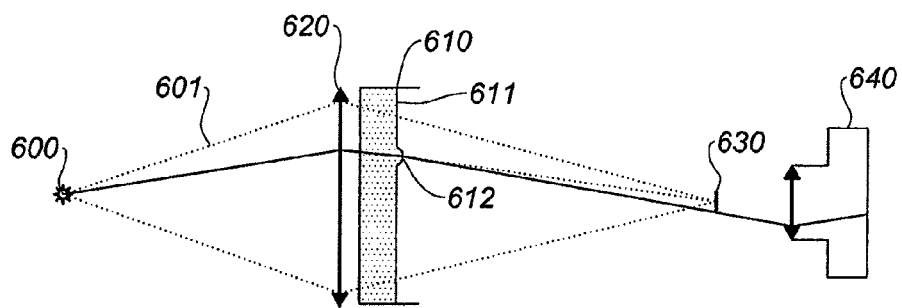
FIGS. 6A-6D show a second variant of the method of the invention, based on the technique of Schlieren photography.

Schlieren photography is an optical method that is itself known and based on the principles of Fourier optics. FIG. 6A shows a Schlieren setup for performing a second implementation of the invention.

A point source 600 emits a diverging beam 601 of substantially monochromatic light that is subsequently focused by an objective lens 620. A transparent Petri dish 610 containing a seeded culture medium having colonies 612 of microorganisms for detection developing on its surface 611 is located immediately downstream from the lens 620 so as to have the focused beam pass therethrough. A mask 630 is arranged in the focal plane of the lens 620. The mask hides all of the light rays coming from the source that have come through the lens and the Petri dish without being deflected. If the surface 611 is perfectly plane and uniform (and within the geometrical optics approximation), then all of the light in the beam 601 would be intercepted by the mask. In reality, surface irregularities 611—including those due to the colonies 612—deflect some of the light rays so that they go past the mask. From the point of view of Fourier optics, it is known that in the focal plane of the lens, a distribution of light is formed that corresponds to the spatial frequency spectrum of the surface 611; the mask thus performs high-pass spatial filtering.

An imaging system (camera 640) is located downstream from the mask and is focused on the surface of the culture medium. The image acquired by the imaging system contains information about the local slope of the surface 611, thus making it possible to reconstruct a three-dimensional sheet of said surface (which, better still, has already been partially subjected to high-pass filtering, without any need for preprocessing).

Given that the mask is of finite dimensions, only those light rays that have been deflected through an angle that is greater than or equal to a threshold value are detected. This threshold value is minimized when the mask presents the same size as the diffraction pattern of the lens. If it is assumed that the source 600 is genuinely a point source (which is always an approximation), then the only local slopes that can be detected are slopes greater than $\lambda/(n-1)d$, where $\lambda$ is the wavelength of the light used, d is the diameter of the lens, and n is the refractive index of the medium. A local slope of angle $\alpha$ deflects light rays through an angle $(n-1)\alpha$, and only deviations greater than the diffraction can be observed. In practice, culture media have surface defects of the order of a few milliradians, which requires a mask that is much greater than this theoretical limit in order to be able to do without any preprocessing. The diameter of the mask needs to be of the order of $(n-1)l^*p_{max}$, where $p_{max}$ is the maximum local slope of surface defects, and l is the distance between the lens and the mask. A micro-colony having a thickness of 1 μm and a diameter of 30 μm imparts a mean local slope to the wave surface of $(1.35-1)/15=23$ milliradians, which is much greater than the surface defects of the gel, and is therefore easy to see. The local slope at the edge of the colony is even greater, typically not less than a few hundreds of milliradians (or a few tenths of a radian).

An advantage of Schlieren photography over geometrical mapping techniques, such as chromatic confocal imaging, is that there is no need to have lateral resolution that is better than the size of the micro-colonies: since a black background is being used, there is no difficulty in detecting and locating items that are smaller than the resolution limit (although naturally it is not possible to separate two items that are closer together than said resolution limit).

Another advantage is that in a single acquisition, the observed field may cover a region that is more extensive than when using the above-described confocal microtopography technique. Thus, acquiring an image by a Schlieren method makes it possible to observe an extensive portion of a Petri dish, or even all of the dish.

In this method, the representation of the topography of the surface of the medium is a two-dimensional representation, i.e. an image, in which variation in intensity between two adjacent pixels represents variation in the altitude of the surface of the illuminated item and/or local variation in its refractive index. The contours that are detected correspond to closed loops that define areas. These loops connect together pixels corresponding to a common variation in gray level.

When the altitude variation between two adjacent pixels is produced by a colony of bacteria, its edge forms an angle relative to the surface of the culture medium that is typically greater than a few tenths of a radian. Such a slope is greater than that formed by the variations in the level of the culture medium, where the angle involved is typically less than 10 milliradians.

Figure 6B:
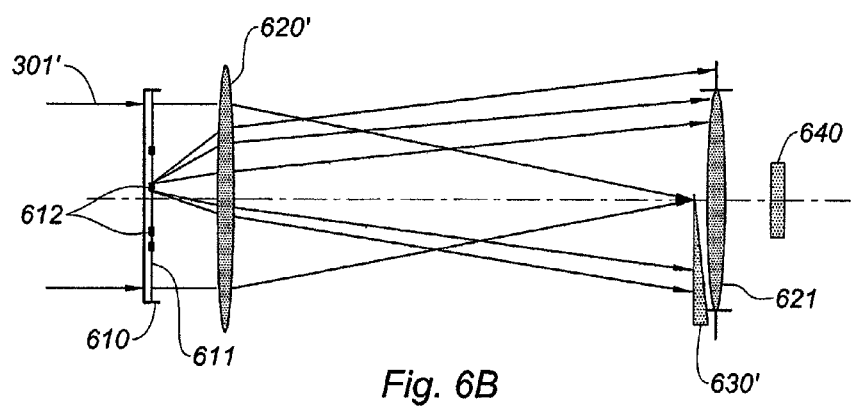

FIG. 6B shows another setup enabling the method of the invention to be implemented by Schlieren photography. Unlike the setup of FIG. 6A, the illuminating beam 301' is collimated when it passes through the transparent Petri dish 610, and it is then focused by a first lens 620' downstream from the dish (focal length of the lens: 200 mm; diameter: 50 mm—these values being given solely by way of example). A second lens 621 (focal length: 10 mm; numerical aperture NA: f/3—once more these values are given solely by way of example) forms an image of the Petri dish. The mask 630' lying in the focal plane of the lens 620' intercepts the light rays that have not been reflected by local slope variations in the observed surface 611, or by local variations of refractive index in said surface (and also those rays that have been deflected downwards, even though that is not essential). When a colony of bacteria develops on the surface 611 of the culture medium, it deflects the light radiation that is incident thereon so that the light does not converge on the mask 630', but is detected by the detector 640 (e.g. a camera having 1400×1000 3 μm pixels). Thus, because colonies of bacteria 612 give rise to local slope fluctuations in the surface 611, they can be detected by the detector 640, in the form of points of light on a black background.

Using a parallel illuminating beam, instead of a diverging/converging beam as in the setup of FIG. 6A, has the effect of making the intensity of the signal independent of the position of the portion of the surface that is being observed. In other words, over the entire observed field, the same local slope in the observed surface produces a signal having the same intensity on the detector, independently of the position of the local slope over the surface 611 of the culture medium 610.

Figure 6C:
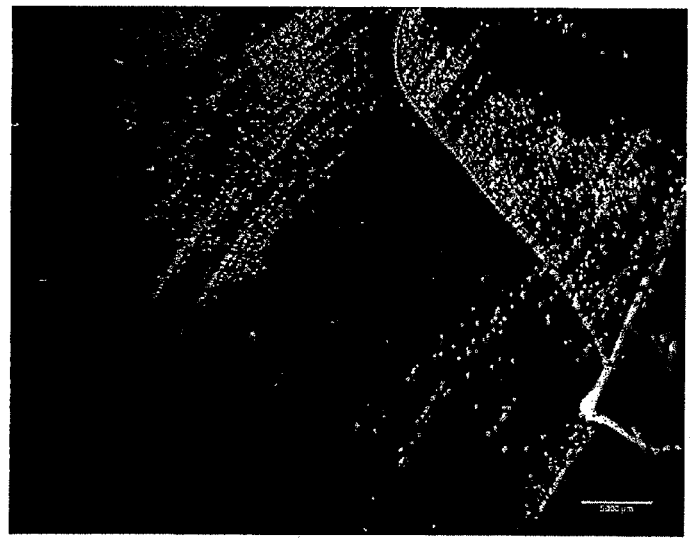

FIG. 6C corresponds to using the FIG. 6B setup to observe colonies of *Escherichia coli* type bacteria eight hours after they have been seeded on the surface of a trypcase soya gelose (TSA) type gelose. The white spots correspond to colonies of bacteria. The continuous line forming a bright right angle in the bottom right portion of the image corresponds to a glass slide constituting a visual reference.

Figure 6D:

FIG. 6D is a photograph of the same culture medium, 24 hours after seeding. It can be seen that there is a good match between the colonies of bacteria photographed in FIG. 6D and those shown in FIG. 6C as detected by transmission Schlieren photography.

Schlieren photography can also be implemented in a reflection configuration, the light source being arranged facing the culture medium, as is the detector. This is appropriate for observing media that are opaque.

Figure 7A:
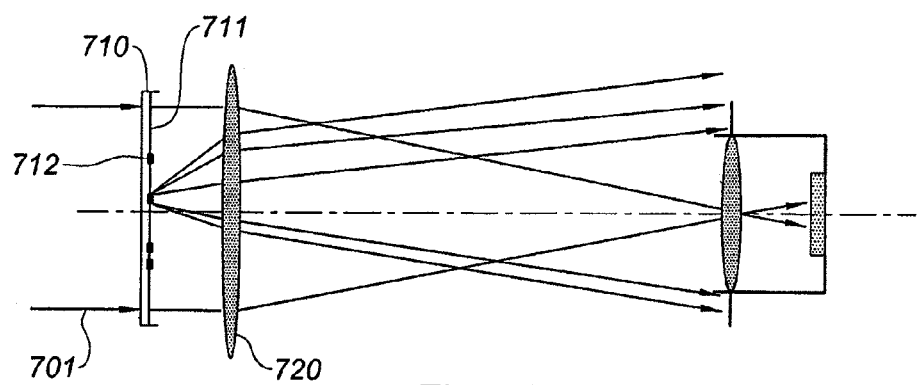
FIGS. 7A-7C show a third variant of the method of the invention based on the technique of ombroscopy.

In another implementation, the colonies of bacteria are observed by a setup implementing the technique of ombroscopy. Such a setup is shown in FIG. 7A. A parallel light beam passes through the Petri dish 710 containing the culture medium, and is then focused on a detector 740 by a first lens 720 (focal length of the lens: 200 mm; diameter: 50 mm—these values being given solely by way of example). When a colony of bacteria 712 develops on the surface 711 of the culture medium, it deflects the light radiation because of the variation in altitude and thus in local slope that is formed on the surface 711. Unlike the Schlieren method, the radiation deflected by a variation in altitude and/or a variation in index on the observed surface is not picked up by the detector 740 (camera having 1400×1000 3 μm pixels, objective lens with a focal length f=10 mm, numerical aperture NA=f/3—these values being given solely by way of example). This device serves to detect a local slope on a plane surface for analysis by virtue of a dark zone appearing in the image formed by the detector 740. Thus, in this method, the colonies of bacteria 712 appear in the form of dark spots on a pale background, which background corresponds to the surface 711 of the culture medium.

As mentioned above on the topic of Schlieren photography, when implementing ombroscopy, the representation of the topography of the surface of the medium is a two-dimensional representation, i.e. an image, in which variation of intensity between two adjacent pixels is representative of a variation in the altitude of the illuminated object surface. It may also represent local variations of refractive index in said surface.

Figure 7B:
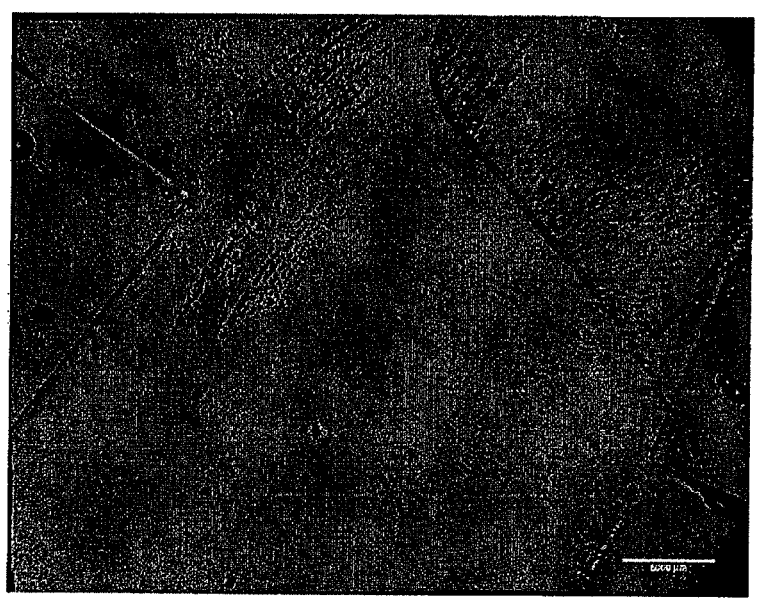

FIG. 7B shows the result of using the setup of FIG. 7A to observe colonies of bacteria of the *Escherichia coli* type eight hours after being seeded on the surface of TSA gelose. The dark spots correspond to the colonies of bacteria. It can be observed that these colonies are in locations that match the results of FIG. 6D (photograph) and the observation shown in FIG. 6C obtained by transmission Schlieren photography.

Figure 7C:
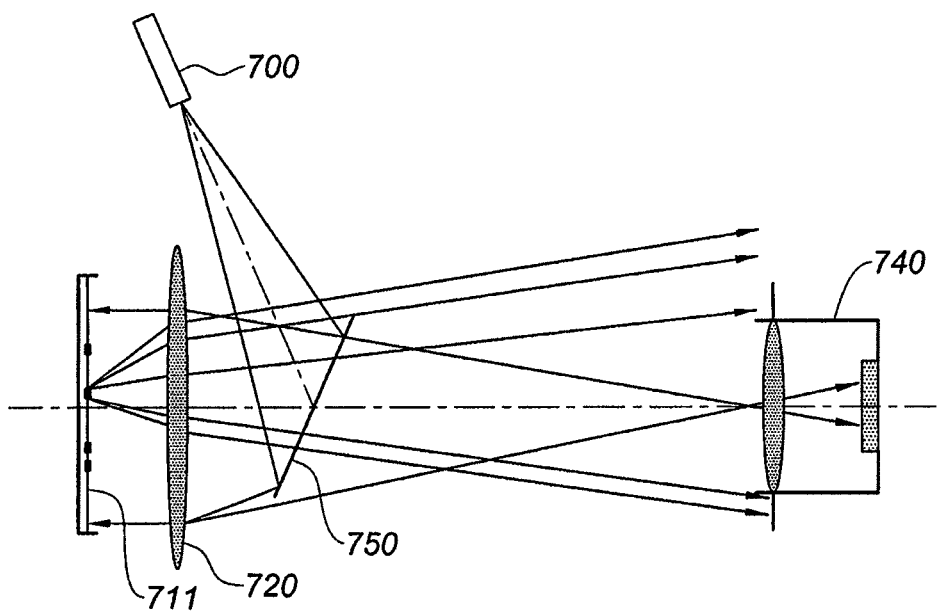

As with the Schlieren technique, it is possible to implement observation of colonies of bacteria by ombroscopy in a reflection configuration, the light source 700 being placed facing the Petri dish 710 containing the culture medium to be observed, as is the detector 740. FIG. 7C shows such a setup, with the light radiation produced by the light source being deflected by a beam splitter 750 and then made parallel by the lens 720. Such a setup is preferred when the culture medium is opaque.

With both Schlieren photography and surface mapping, it is advantageous to make use of any methods of image processing and of subtracting consecutive images that are suitable for revealing modifications due to growth.

Once the locations of the clusters have been identified, the bacteria can themselves be identified using known measurements, e.g. by in-situ analysis (diffraction, Raman spectrometry), or by other methods of analysis, such as mass spectrometry. Under such circumstances, the analysis is performed ex-situ and therefore requires the colony of bacteria to be removed.

Location by topography may make it possible, for example, to select clusters of volume that exceeds a certain threshold, the selected clusters subsequently being subjected to qualitative analysis.

The invention is not limited to detecting colonies of microorganisms on the surface of a culture medium. The surface on which the biological clusters, and more generally the biological particles, for detection are located may equally well be a solid, e.g. a substrate of glass or of functionalized silicon, or a microporous filter used for recovering bacteria obtained in a filtered liquid and possibly, but not necessarily, being suitable for placing on a culture medium. The preprocessing operations implemented during the second step E2 of the method are preferably adapted to the type of surface under consideration.

The ambient medium lying above the surface may be a vacuum or a fluid such as a gas or a liquid, with a gas and in particular air being preferred. The ambient medium may be confined, so as to avoid risks of contamination, and also risks of the gelose evaporating, where applicable.

The invention claimed is:

1. A method of detecting a cluster of biological particles on a surface, the method comprising the steps:
    a) determining a topographical representation of said surface; and
    b) detecting in said topographical representation at least one contour defining a region that potentially corresponds to a cluster of biological particles;
    these steps being implemented with the help of electronic data processor means.

2. A method according to claim 1, wherein said biological particles are selected from microorganisms, vegetable, and animal cells.

3. A method according to claim 1, wherein said biological particles present a diameter or a main dimension that is less than or equal to 100 µm.

4. A method according to claim 1, wherein said surface is selected from the group consisting of the interface between a culture medium and a surrounding medium, the surface of a functionalized substrate, and the surface of a microporous membrane.

5. A method according to claim 1, wherein said step a) consisting in determining a topographical representation of said surface is implemented by an optical method performed without contact and without preparing the sample.

6. A method according to claim 5, wherein said step a) consisting in determining a topographical representation of said surface is implemented by chromatic confocal microtopography.

7. A method according to claim 5, wherein said step a) consisting in determining a topographical representation of said structure is implemented by Schlieren photography or by ombroscopy.

8. A method according to claim 1, wherein said step b) consists in detecting at least one contour is implemented by measuring the local slope of said topographical representation of the surface, with thresholding.

9. A method according to claim 1 also including an operation of preprocessing said topographical representation, the preprocessing operation comprising detecting a reference surface and subtracting it.

10. A method according to claim 1, including repeating steps a) and b) at successive times, and selecting only those regions identified in the steps b) that are of shape or size that varies over time.

11. A method according to claim 1, including an additional step c) consisting in evaluating the quantity of biological particles present in a cluster.

12. A method according to claim 2, including an additional step of in-situ or ex-situ identification of the microorganisms arranged in clusters.

\* \* \* \* \*